United States Patent
Vogel et al.

(10) Patent No.: US 7,375,335 B2
(45) Date of Patent: May 20, 2008

(54) EFFECT-PARTICLE ORIENTATION AND APPARATUS THEREFOR

(75) Inventors: Randall Allen Vogel, Wilmington, DE (US); John C. Modla, Hockessin, DE (US); Edward J. Delawski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 403 days.

(21) Appl. No.: 10/960,825

(22) Filed: Oct. 7, 2004

(65) Prior Publication Data

US 2005/0083529 A1  Apr. 21, 2005

Related U.S. Application Data

(60) Provisional application No. 60/509,439, filed on Oct. 7, 2003.

(51) Int. Cl.
*G01J 5/02* (2006.01)
(52) U.S. Cl. .............. 250/341.8; 250/339.07; 250/339.11; 356/445; 356/446
(58) Field of Classification Search ......... 250/341.8, 250/339.07, 339.11; 356/445, 446
See application file for complete search history.

(56) References Cited

U.S. PATENT DOCUMENTS

| | | |
|---|---|---|
| 3,690,771 A | 9/1972 | Armstrong, Jr. et al. |
| 4,479,718 A | 10/1984 | Alman |
| 4,569,887 A | 2/1986 | Cowles |
| 4,692,481 A | 9/1987 | Kelly |
| 4,711,580 A | 12/1987 | Venable |
| 4,755,058 A | 7/1988 | Shaffer |
| 4,900,611 A | 2/1990 | Carroll, Jr. |
| 4,917,495 A * | 4/1990 | Steenhoek .............. 356/328 |
| 5,231,472 A | 7/1993 | Marcus et al. |
| 5,367,379 A * | 11/1994 | Makino ................... 356/446 |
| 5,494,954 A | 2/1996 | Das et al. |
| 5,583,642 A * | 12/1996 | Nakazono ............... 356/405 |
| 5,587,427 A | 12/1996 | Abe et al. |
| 5,653,927 A | 8/1997 | Flynn et al. |
| 5,815,279 A | 9/1998 | Lex |
| 6,064,487 A | 5/2000 | Kettler et al. |
| 6,113,838 A | 9/2000 | Flynn et al. |

(Continued)

FOREIGN PATENT DOCUMENTS

JP  2281045  11/1990

(Continued)

OTHER PUBLICATIONS

Germer, Thomas A. et al., "Modeling the Appearance of Special Effect Pigment Coatings", Pub. Surface Scattering & Diffraction for Advanced Metrology, SPIE 4447, 77-86 (2001).

(Continued)

*Primary Examiner*—Dave Porta
*Assistant Examiner*—Yara B Green

(57) ABSTRACT

A method and apparatus for determining the effect-particle orientation in a film or coating are disclosed. The method comprises using opposing directional reflectance measurements, preferably in continuous processes and allows for an on-line evaluation system to provide more specific control over particle orientation, thereby allowing for better color matching between and among various panels or articles.

23 Claims, 2 Drawing Sheets

U.S. PATENT DOCUMENTS

| | | | |
|---|---|---|---|
| 6,292,264 | B1 | 9/2001 | Voye et al. |
| 6,526,369 | B1 | 2/2003 | Meinecke et al. |
| 7,023,555 | B2 * | 4/2006 | Kubitzek .................... 356/445 |
| 2001/0036309 | A1 | 11/2001 | Hirayama et al. |
| 2002/0167669 | A1 * | 11/2002 | Schwarz .................... 356/446 |

FOREIGN PATENT DOCUMENTS

| | | |
|---|---|---|
| JP | 9253559 | 9/1997 |
| JP | 9273962 | 10/1997 |
| WO | WO 87/07381 | 12/1987 |
| WO | WO9936477 | 7/1999 |

OTHER PUBLICATIONS

Denne, Ingrid "Microscopic Evaluation of Effect . . . Color Matching," Presented at CPMA Conference "Color Pigments for the New Millennium" Charlotte, NC Apr. 17-19, 2000.

PCT International Search Report for International application No. PCT/US2004/033426, dated Mar. 11, 2005.

* cited by examiner

EFFECT-PARTICLE ORIENTATION AND APPARATUS THEREFOR

This application claims the priority if provisional U.S. application 60/509,439, filed Oct. 7, 2003, the entire disclosure of which is incorporated herein by reference.

FIELD OF INVENTION

The present invention relates to a method and apparatus for determining the effect-particle orientation such as in a film or coating.

BACKGROUND OF THE INVENTION

Effect-particle orientation and its impact on appearance properties has been the subject of study within the paint industry for many years. Colorimeters and spectrophotometers are well known in the art and are used to measure certain optical properties of various paint films which have been coated over test panels. A spectrophotometer provides for the measurement of the amount of light reflected at varying light wavelengths in the visible spectrum by a painted panel that is held at a given angle relative to the direction of an incident source of light. The reflectance factor of the paint enables paint chemists to calculate color values by which to characterize various paint colors. For a paint containing no light-reflecting flakes or particles, the reflectance factor does not vary with the angle of the panel relative to the direction of the incident light except at the gloss (specular) angle.

Typical effect-particles, for example metallic or pearlescent flakes, mica or other non-spherical particles, are often utilized in paints and coatings to provide a distinctive or appealing appearance because such particles can impact the visual perception of the painted or coated surface. These particles can accentuate the appearance aspects of a substrate such as its curvature, color appearance and color intensity, which may change according to the viewing angle, a desired visual effect for substrates such as automotive panels. Ideally, flat particles provide the greatest change in color per a change in the viewing angles, whereas particles approaching a spherical shape provide the least color change with a change in the viewing angle.

Some continuous sheet and film processes include the use of effect flake particles. However, particle orientation is variable and either not monitored or unable to be monitored, beyond a visual investigation and perspective. This process has been able to achieve a visual effect, but these effects are a result of being imparted in an uncontrolled fashion. It is a very difficult, and somewhat haphazard, method of attempting to match (both visually and color-wise) metallic painted panels and sheet color using pigments and metallic pigments.

In the paint coatings industry using conventional technology, the orientation of the effect-particles is to measure the light reflection at multiple angles in a single determination (i.e., in one direction). The resultant measurement, with a subsequent calculation, provides an indication of the color appearance in a qualitative manner for the specific color being tested. Thus, the color appearance can then be compared and changed or adjusted if necessary. However the use of only a single absolute measurement is problematic because it does not provide a direct determination for identifying when an effect-particle is flat or parallel to a surface. Additionally, the single "flop calculation" method does not provide relative particle orientation suitable for in-process adjustments. Furthermore, outside influences may affect this calculated value, inferring the effect-particles are flat (usually maximizing the "flop" calculation).

Another disadvantage of conventional technology is that the processes known in the art work in a batch-like manner, where the use of a stationary panel having no vibrations is required to provide satisfactory data, and therefore, are too slow to provide adequate control feedback in many continuous processes, particularly plastic sheet processes. As a result, these processes are burdensome, time consuming, not cost effective and thus, not for use with continuous processes.

Thus, it would be desirable to have a process or apparatus capable of taking opposing directional reflectance measurements for an indication of effect-particle orientation in continuous processes, thereby allowing for better control of effect-particle orientation, which is necessary to maintain the appearance consistency of a substrate. Such process or apparatus preferably has the ability to exert greater control over the effect-particle orientation relative to the surface of the effect-particle-containing material as well as controlling the process of the sheet or film melt process, thereby improving the uniformity of sheet polymer orientation. Such process or apparatus provides for greater consistency of appearance when the effect-particle-containing material (e.g. paint, film, coating, coated article or polymer) is viewed at similar angles in opposite directions and between different articles made from the same sheet or film; greater repeatability of particle orientation from one manufacturing campaign to another; and can provide unique orientation characteristics through changing process conditions to provide nearly similar reflection characteristics in opposing directions, or very different reflection characteristics in opposing directions.

SUMMARY OF THE INVENTION

The invention comprises embodiments for an article and a process for measuring the reflectance, and thereby measuring effect-particle orientation, in a continuous process such that the effect-particle-containing material is moving and/or vibrating. The process comprises (a) illuminating a surface of an effect-particle-containing material using incident beams of light in opposing directions over substantially the same given area (preferably the incident beams of light are emitted in both the upstream and downstream machine directions);

(b) measuring incident light reflectance from the effect-particle-containing material in opposing directions;

(c) determining a first absolute value of a difference between the opposing reflectance measurements at corresponding angles (a strategy to increase or decrease particle tilt in die flow direction);

(d) comparing the first absolute value obtained in step (c) to a second absolute value obtained from a known standard; and optionally (e) manipulating the effect-particle orientation to minimize, maximize or otherwise adjust the difference between the first and second absolute values.

The invention also comprises an apparatus capable of determining the incident light reflectance in opposing directions and thus effect-particle orientation. The apparatus comprises (i) a reflectance head, having a body that defines a reflectance zone and a plurality of apertures;

(ii) optionally at least a first and second light source in opposing positions and at least a first and second light detector inserted into the reflectance head apertures, wherein for each light source there is a corresponding opposing detector; and (iii) optionally a means for interpreting received light, which is in communication with said light detectors, from the at least first and second light detectors, for calculating a light reflectance factor.

DETAILED DESCRIPTION OF THE INVENTION

Figure 1:
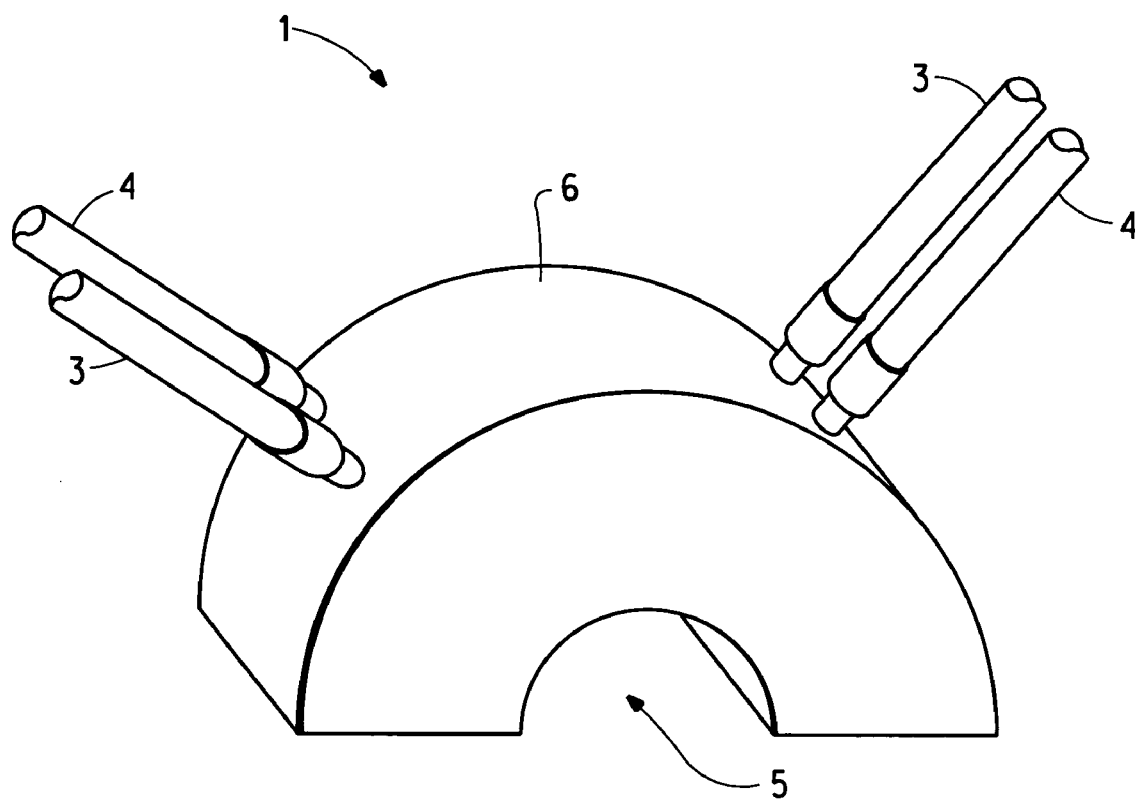
FIG. 1 depicts an embodiment of an assembly of a reflectance head, light sources and detectors, and reflectance zone according to the present invention.

All patents, articles or other publications or disclosures described in this application are hereby incorporated by reference herein in their entirety.

With respect to the ranges set forth herein, unless otherwise noted, any combination of values may be used that are within the minimum and maximum values set forth in the given ranges.

The embodiments of the invention may be used in conjunction with effect-particle-containing materials (e.g. paint, film, coated substrates or articles having light-reflecting particles or flakes); as well as providing an indication of polymer flow, and therefore to an extent, indicate the orientation of the polymer melt.

As used herein, the term "effect-particle", means to describe any particle capable of providing a visual color change as the viewing angle changes; "flop" refers to the difference in color and appearance of a material viewed over two different viewing angles; "flop angle" refers to the viewing angle when a material is viewed from a direction far from the specular, typically 70 degrees or more, normally associated with a change in color and appearance at two viewing angles; "appearance" refers to the manifestation of the nature of the article, film or coating through visual attributes such as size, shape, color, texture, glossiness, transparency, opacity and the like; "matching" refers to providing, by formulation adjustment or other means, a trial color that is indistinguishable from, or within specified tolerances of, a specified standard color under specified conditions; and "continuous process" includes continuous polymer fabrication technologies such as sheet or film casting, roll gap nipping or calendaring processes utilized in appearance panels, laminating processes, coating processes and continuous profile extrusion processes (processes combining polymer melts in a co-extrusion of multiple layers for appearance panels) as well as continuous coating processing technologies such as the painting, printing or coating of an effect-particle-containing material (i.e. paper, metal, polymers and the like), where the coating contains effect-particles.

Manufacturing of appearance panels is often done in a continuous process. In these processes, multiple manufacturing variables may impact the effect of particle orientation and the high speed of today's processes necessitate the use of an on-line evaluation system to provide more specific control over particle orientation, thereby allowing for better color matching between and among various panels or articles.

Typically the embodiments of the present invention may be utilized in evaluating any effect-particle-containing material (e.g. paint, film, polymer, or other coating containing light-reflecting flakes or particles). The issues regarding the fabrication of appearance panels is not limited to the paint industry and encompasses monolayers and multi-layered panels of different polymer materials, wherein various polymer layers are combined to deliver particular appearance properties to an article. These types of panels include ionomer surfaced paint laminates formed as decorative panels, wherein these laminates require high visual consistency in appearance between panels as well as consistency in appearance when viewing them from the upstream and downstream directions.

One characterization of light-reflecting particles or effect-particles, which includes flakes, may be determined by their light reflectance, particularly with respect to those effect-particles that are flat and parallel to the surface of the effect-particle-containing material. The light-reflecting particles or effect-particles incorporated into and onto the film and/or coating and/or articles reflect light directionally rather than in a diffuse manner. The directional reflectance characteristic of, for example, a paint film or other coating, results in a phenomenon known as goniochromatism, which is also referred to as "flop". Thus, the color of a paint or coating containing light-reflecting particles may change in appearance when viewed at varying angles. To characterize a decorative panel for this directional or angular reflectance (i.e., flop), the determined reflectance factors are measured at multiple angles and used in a formula to determine a "flop number", which can characterize an appearance. The assumption of this single multi-angle measurement and flop number calculation is that effect-particles are oriented parallel and are flat relative to the surface of the effect-particle-containing material. Under this assumption, a second reflectance measurement following rotation of the measuring instrument relative to the surface of the effect-particle-containing material can also result in a similar "flop number" characterization.

When the collective effect-particle orientation is not flat and parallel to the surface of the effect-particle-containing material, a single multi-angle measurement characterization may vary as the instrument orientation relative to the surface changes, thereby rendering the characterization less useful. The embodiments of the invention provide information regarding relative orientation of the effect-particles in a flow field. Light reflectance detection and comparison in opposing directions provides relative information regarding effect-particle orientation. Where the effect-particle orientation is parallel to the surface of the effect-particle-containing material, the absolute value difference between reflectance factors from opposing, but same angle reflections, is minimized. As the orientation of the effect-particles deviates from the parallel position relative to the surface of the effect-particle-containing material, the reflectance factor difference increases.

The reflectance factor of a film or coating is identified as the ratio of the light flux reflected from the sample to the light flux reflected from a perfect reflecting diffuser when the sample and perfect diffuser are identically irradiated with the light source. A perfect white reflector has a value of 1, whereas a perfect black non-reflector has a value of zero.

The embodiments of the invention provide a technique and instrument suitable for use in continuous processing systems to characterize particle orientation for on-line feedback control in adjusting particle orientation; for matching color using processing conditions with appropriate pigments and metallic particles to color match metallic paint panels and the like; and for greater control of the effect-particle orientation so that effect-particle flatness can be maximized, minimized or any position in between. This maximization of effect-particle flatness can be desirable in some industries because if flake orientation, relative to the effect-particle-containing material's surface, is not flat (or parallel to the sheet or film surface) it results in a noticeable difference in appearance when a painted panel is adjacent to a pigmented sheet or film, particularly when the viewing orientation is changed significantly. The embodiments of the invention allow for the determination or measurement of effect-particles having any orientation such that an effect-particle orientation is determinable.

The embodiments of the invention also provide feedback information based on reflectance measurements performed in opposing directions, preferably upstream and downstream machine directions, for single (e.g. opposing light sources positioned at substantially the same illumination angle) or multiple (e.g. opposing light sources positioned at differing illumination angles) angle measurements of reflectance, as further described below. As a result, the measured difference determined can be utilized to adjust the parameters controlling the process, for example if flat flake orientation (or flakes parallel to the film surface) is desired, the difference between the reflectance measurements at corresponding angles in the opposing directions is preferably minimized.

The embodiments of the present invention can also be used to characterize an appearance in the effect-particle-containing material's cross machine direction or in a direction about 90 degrees from the machine direction.

An effect-particle having an orientation that is parallel to the surface can provide a minimum absolute value of the calculated difference between the opposing (preferably upstream and downstream machine direction measured reflectance values) measured reflectance values at a consistent angle of measurement. Average effect-particle orientation that is not parallel to the film surface may have an increasing difference in the reflectance absolute value between the opposing measurement directions and shows an increasing difference as the particles' orientation deviates farther away from a flat or parallel position relative to the surface to a perpendicular orientation.

Generally, the incident light reflectance from the effect-particle-containing material in opposing directions is measured and, as noted above, a first absolute value of a difference between the opposing reflectance measurements at corresponding angles is determined. The first absolute value can then be compared to a second absolute value obtained from measuring the incident light reflectance of a known standard (preferably where the first and second absolute values were obtained using the same parameters with respect to the light source angle, viewing angle and the like). The known standard may be any previously obtained absolute value determined from measurements taken from a different effect-particle-containing material (preferably to match color between or among effect-particle-containing materials such as decorative panels) or a previous measurement taken within the same effect-particle-containing material.

The present invention can utilize the reflectance measurements as an indication of polymer flow, and therefore to an extent, indicate the orientation of the polymer melt. This data may be suitable for controlling sheet parameters that affect polymer orientation. Thus, the differences in flow rate, particularly through a set of nip rollers utilized for polymer melt calendaring, induce localized differences in orientation in the sheet, which may be a variable for end use properties. Therefore, improving control over the polymer melt processing may provide a corresponding improvement in downstream sheet properties and utilities. Monitoring the reflectance of particles in the sheet may provide an improved means to monitor polymer orientation and therefore allow for better control over process variables such as layer temperatures entering the die and/or nip gap adjustments relative viscosities of adjacent layers, size of the rolling bank or nip pressure, particularly through the nip or calendaring process.

The apparatus can allow for beams of light to be projected or emitted to the surface of the effect-particle-containing material (e.g. film, polymer melt, coating or article) via the at least first and second light sources. These light sources can be positioned at the same or substantially the same angle in opposing directions relative to the surface of the effect-particle-containing material being evaluated, so that substantially equal incident angles of light on the surface are obtained. The flakes or particles in the effect-particle-containing material reflect the light upward at a given angle (dependent upon the angle at which the light is projected or emitted), wherein the magnitude of the reflected light is a function of the orientation of the flakes or particles. The reflected light is collected in the reflecting zone of the reflectance head and enters the light detector. The light detector typically has an optical axis coincident with the longitudinal axis of the reflected beam. In measuring the incident light reflectance, the light detector allows for the relay of information to the means for interpreting the received light, which converts the reflected light into an electronic signal that can be electronically processed for comparison to the electronic signal received from a known reference standard, wherein subsequently, the reflectance factor can be calculated using conventional methods known by those skilled in the art.

Figure 2:
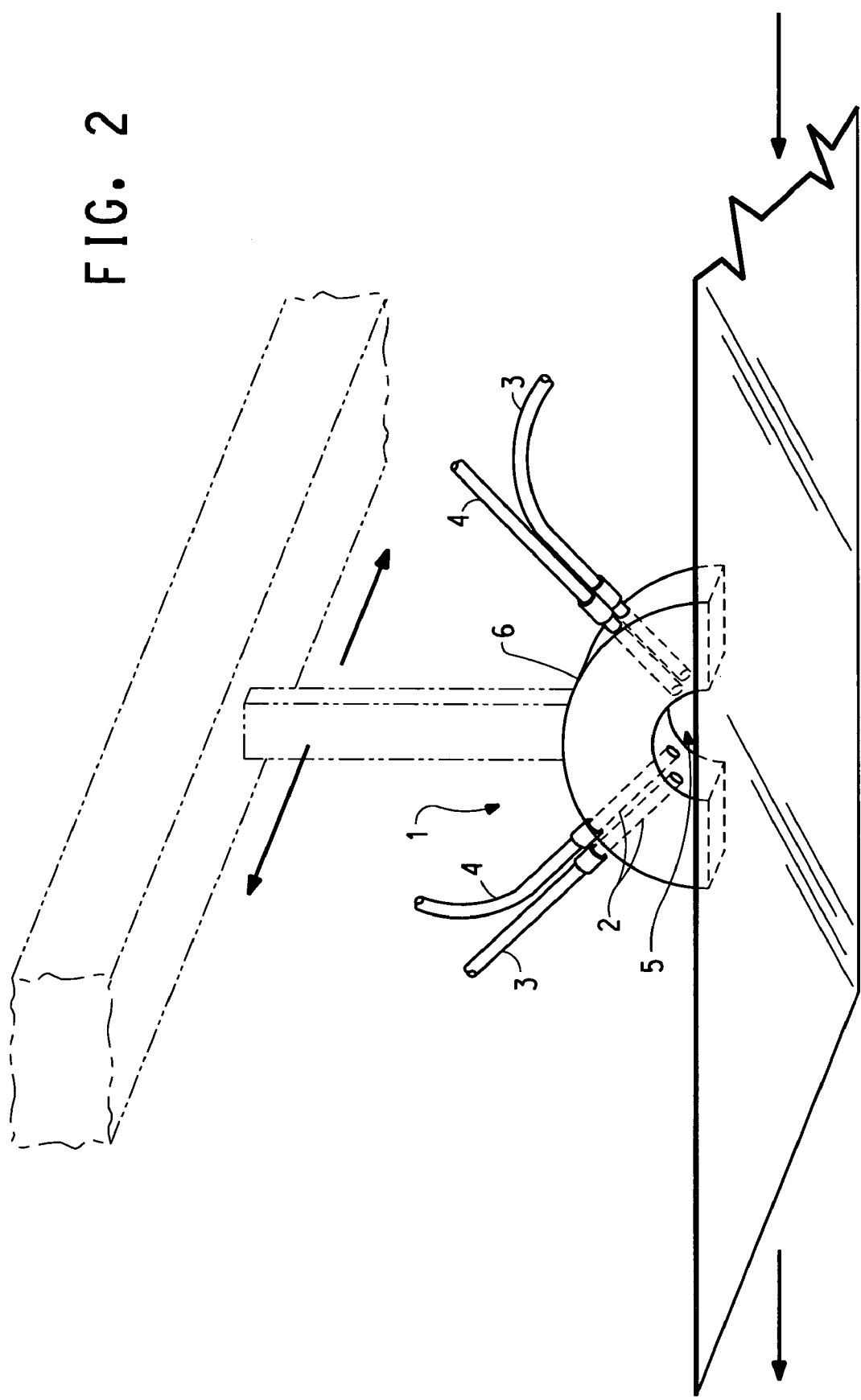
FIG. 2 depicts an embodiment that is suspended above an effect-particle-containing material.

Referring to FIGS. 1 and 2, the reflectance head (1) comprises a body (6) having a plurality of apertures (2) which allow for the insertion of at least the first and second light sources (3) and at least first and second light detectors (4), wherein the light sources and detectors have entrance into the reflecting zone (5). The reflecting zone preferably has a concave configuration, thereby allowing the light detectors to gather any reflected light for determination of the reflectance factor. The reflecting zone is positioned towards the surface of the effect-particle-containing material (e.g. paint film, coating, polymer melt or other coated article).

The reflectance head (1) can be a floating head, such that its design allows it to be positioned above the effect-particle-containing material, while also traversing the entire cross width of the film or sheet being evaluated. The cross width monitoring may be either on a continuous basis or intermittent basis with frequent measurements for particle orientation, due to high variability of flake or particle tilt across the sheet width. Processing variables can change particle orientation over a short time span and across narrow areas of the sheet, so it is preferred to monitor either continuously or frequently to identify any changes in flake or particle for potential correction.

The reflectance head (1) can be located at a fixed elevation above the effect-particle-containing material being evaluated, wherein preferably the distance is about 0.040 inches (1.016 mm).

Generally, the material for use in the body (6) of the reflectance head (1) can be made from any material. Preferably, the body is made from Teflon® (a tetrafluoroethylene fluorocarbon polymer) or other similar composition because these materials may not or only minimally damage the paint film or coating if the head comes into contact with the effect-particle-containing material.

The at least first and second light sources (3) can be those conventionally known within the art capable of providing the necessary light at the appropriate wavelengths (e.g. the OPTEK OP290 diode available from OPTEK Technologies, Carrollton Tex.), where the light is transmitted for projection onto the effect-particle containing material's surface by fiber optic cable (i.e. cables having part number S8-120TS-G available from Cuda Products of Jacksonville, Fla.) capable of emitting non-visible light, preferably in the Near-Infrared (NIR) spectrum, more preferably light of about 940 nanometers. The invention can utilize non-visible light because when evaluating color films, it allows the apparatus to retain its sensitivity.

As shown in the Figures, the at least first and second light sources (3) and at least first and second light detectors (4) (e.g. the OPTEK OP5599 available from OPTEK Technologies, Carrollton Tex.) are preferably positioned adjacent (in either an upstream or downstream position) to one another. The first light source can be in an opposing position relative to the second light source. Also, each detector can be in an opposing position in relation to its corresponding light source. Alternatively, the light sources and opposing detectors may be offset from one another due to area constraints.

The incident light reflected from the surface of the effect-particle-containing material being evaluated can be varied depending upon the nature of the effect-particle-containing material, light sources and detectors. The light sources (the at least first and second light sources (3)) may be positioned at any angle relative to the surface of the effect-particle-containing material. Preferably, the light sources may be positioned from about 10 degrees from the horizontal axis of the surface of the effect-particle-containing material to about 10 degrees short of the perpendicular vertical axis. The light detectors are preferably positioned at a viewing angle that deviates from the specular angle of the incident light.

The light sources may be positioned at multiple angles, for example, where a first light source is positioned at an angle of about 15 degrees relative to the surface of the effect-particle-containing material, while a second incident light source is position at an angle of about 45 degrees relative to the surface of the effect-particle-containing material. The use of at least a first and second opposing light source, each positioned at the same angle relative to the surface of the effect-particle-containing material is preferred. The detectors are preferably positioned at the same viewing angle.

The means for interpreting the electronic signals generated in response to the detection of light can be an electronics processing box (suitable examples available from Creative Micro Designs of Newark, Del., for example the Dual Channel Flake Orientation Measurement instrument, Dual Channel Analyser with RS232). This electronics processing box can process an electronic signal for comparison to the electronic signal received from a known reference standard, wherein subsequently, the reflectance factor can be calculated. The processing box may be any one of the conventionally known devices capable of performing the necessary processing needs described herein. As disclosed above, the electronic signal can be electronically processed, using conventional methods known by those skilled in the art, for comparison to the electronic signal received from a known reference standard for the calculation of the reflectance factor.

The following Examples are for illustration only and are not to limit the scope of the invention.

EXAMPLES

In the Examples, Tables 1, 2 and 3 contain data pertaining to color readings with flop and flop difference calculations. In the Tables the following designations were used:

+MD, wherein the light was emitted in the downstream machine direction and designated at 0°;

−MD, wherein the light was emitted in the upstream machine direction and designated as 180°, such that the +MD light and −MD light were emitted in opposing directions;

+TD, wherein the light was emitted perpendicularly to the downstream machine direction and designated as 90°; and −TD, wherein the light was emitted perpendicularly to the upstream machine direction and designated as 270°, such that the +TD light and −TD light were emitted in opposing directions.

Example 1

An ionomer paint film laminate made in a sheet extrusion process with an amythest pigment color in the second layer was measured for color flop calculations over a small area with a Chromavision™ MA 100 color instrument available from X-Rite, Inc. A small square was cut from the sheet (4" side) and rotated 180 degrees and placed on the larger sheet near where it was cut out. The small square and adjacent larger area had visually different color appearances.

Example 2

An ionomer paint film co-extrusion laminate was made on a multi-layer sheet line. Frequent measurements of color for flop calculations were measured in both the upstream and downstream directions. Differences in flop were calculated for each set. Process adjustments were made which increased and decreased flop differences. The color for samples made with low flop difference matched closely in both upstream and downstream viewing directions. The sample colors made under high flop difference conditions showed significantly different appearance in both lightness and color when viewed in upstream and downstream appearance.

Example 3

Opposing direction measurements were taken across the width of an ionomer laminate (Runs 1 and 2). Likewise measurements were taken in an MD "lane" of the web with the following flop difference calculations.

TABLE 1

Color readings with flop & flop difference calculations.
RUN 1
Sheet ID - middle of sheet
Color - Bright Silver

| Color Readings: | L | a | b |
| --- | --- | --- | --- |
| +MD readings - 0° | | | |
| 15° | 93.06 | 0.66 | 0.49 |
| 45° | 49.26 | 0.52 | 0.63 |
| 110° | 39.71 | 0.52 | −1.68 |

TABLE 1-continued

Color readings with flop & flop difference calculations.
RUN 1
Sheet ID - middle of sheet
Color - Bright Silver

| Color Readings: | L | a | b |
|---|---|---|---|
| +TD readings - 90° | | | |
| 15° | 106.9 | 0.47 | 1.51 |
| 45° | 53.22 | 0.68 | 0.93 |
| 110° | 40.27 | 0.44 | −1.58 |
| −MD readings - 180° | | | |
| 15° | 109.38 | 1.48 | 3.59 |
| 45° | 52.25 | 0.81 | 1.48 |
| 110° | 40.24 | 0.48 | −1.5 |
| −TD readings - 270° | | | |
| 15° | 106.88 | 0.71 | 1.99 |
| 45° | 53.5 | 0.73 | 0.96 |
| 110° | 40.44 | 0.42 | −1.63 |

Flop Formula = $(2.69*(L_{15}-L_{110})^{1.11})/(L_{45}^{0.86})$
Flop (+MD) = 7.786
Flop (−MD) = 9.870
Flop (+TD) = 9.324
Flop (−TD) = 9.253
Flop Difference (+MD − (−MD)) = −2.1 (Absolute Value = 2.1)

TABLE 2

Color readings with flop & flop difference calculations
RUN 2
Sheet ID - operator side of sheet
Color - Bright Silver

| Color Readings: | L | a | b |
|---|---|---|---|
| +MD readings - 0° | | | |
| 15° | 99.04 | 0.72 | 1.08 |
| 45° | 50.02 | 0.36 | 0.42 |
| 110° | 39.47 | 0.07 | −2.47 |
| +TD readings - 90° | | | |
| 15° | 107.64 | 0.47 | 1.11 |
| 45° | 53.53 | 0.59 | 0.66 |
| 110° | 39.82 | 0.11 | −2.13 |
| −MD readings - 180° | | | |
| 15° | 106.67 | 1.07 | 2.37 |
| 45° | 51.04 | 0.52 | 0.88 |
| 110° | 39.07 | 0.08 | −2.35 |
| −TD readings - 270° | | | |
| 15° | 110.37 | 0.49 | 1.75 |
| 45° | 53.74 | 0.66 | 0.85 |
| 110° | 40.25 | 0.14 | −2.09 |

Flop Formula = $(2.69*(L_{15}-L_{110})^{1.11})/(L_{45}^{0.86})$
Flop (+MD) = 8.685
Flop (−MD) = 9.822
Flop (+TD) = 9.462
Flop (−TD) = 9.785
Flop Difference (+MD − (−MD)) = −1.1 (Absolute Value = 1.1)

Example 4

An ionomer multi-layer decorative sheet produced in an extrusion sheeting process with a bright silver appearance was measured with a multi-angle spectrophotometer, a ChromaVision™ MA100 built by X-Rite, Incorporated of 3100 44th Street SW, Grandville, Mich. 49418. The sheet construction is shown below. Color readings on the sheet sample are shown in Table 3.

Sheet Construction
Sample ID: FCL020501-2
Color: Bright Silver

Layer 1—the material was an ionomer made from partially neutralizing an ethylene acrylic acid copolymer with metal ions available as Surlyn® from E. I. duPont de Nemours and Company. The level of acid neutralization (a combination of acid level and neutralization extent) of the ionomer is such as to provide good scratch/mar performance with high clarity. Additives are added to provide for better outdoor exposure weathering durability. Layer 1 had a thickness of 0.006 inches and contained no pigment.

Layer 2—the material was similar to Layer 1, however different additives were included. Layer 2 had a thickness of 0.012 inches and contained Silvet 790-20-E pigment, which is an aluminum flake paste concentrate made by Silberline.

Layer 3—the material was Exact 8201, which is a very low density polyethylene (mVLDPE) produced with metallocene catalyst. More specifically it is an ethylene octane copolymer made in a metallocene process by ExxonMobil Chemical Company. Layer 3 had a melt index of 1.1 g/10 minutes, a specific gravity of 0.88, and a thickness of 0.002 inches and contained no pigment.

Layer 4—the material was Bynel 50E739, which is an anhydride modified polypropylene resin manufactured by E. I. duPont de Nemours and Company having a melt flow rate of 6 (ASTM D1238, 230 C./2.16), a density of 0.89 g/cm$^2$, a melt point of 142 C. and a thickness of 0.007 inches and containing no pigment.

TABLE 3

Color readings with flop & flop difference calculations
Sheet ID - FCL020501-2 retainer 8½" × 11" middle of sheet piece
Color - Bright Silver

| Color Readings: | L | a | b |
|---|---|---|---|
| +MD readings - 0° | | | |
| 15° | 106.60 | 1.47 | 3.6 |
| 45° | 41.28 | 0.25 | 1.84 |
| 110° | 27.75 | −0.62 | 0.19 |
| +TD readings - 90° | | | |
| 15° | 119.66 | 1.25 | 2.96 |
| 45° | 50.66 | 0.20 | 1.92 |
| 110° | 32.93 | −0.55 | 0.38 |
| −MD readings - 180° | | | |
| 15° | 122.09 | 1.99 | 5.38 |
| 45° | 44.28 | 0.48 | 2.64 |
| 110° | 28.17 | −0.55 | 0.11 |
| −TD readings - 270° | | | |
| 15° | 121.16 | 1.27 | 2.94 |
| 45° | 51.13 | 0.23 | 1.95 |
| 110° | 32.86 | −0.56 | 0.38 |

Flop Formula = $(2.69*(L_{15}-L_{110})^{1.11})/(L_{45}^{0.86})$
Flop (+MD) = 9.7
Flop (−MD) = 10.9
Flop (+TD) = 8.7
Flop (−TD) = 8.8
Flop Difference (+MD − (−MD)) = 9.7 − (10.9) = −1.2 (Absolute Value = 1.2)

What is claimed is:

1. An apparatus comprising a reflectance head, a plurality of apertures, light sources, and light detectors wherein
the reflectance head comprises a body and a plurality of apertures and the body defines a reflectance zone;
the light source comprises at least a first light source and a second light source wherein the first light source and the second light source are in opposing positions positioned at substantially the same illumination angle;
the light detector comprises at least a first light detector and a second light detector; and
the first light source and the second light detector are located in different planes.

2. The apparatus of claim 1 further comprising at least a first light detector and a second light detector inserted in the apertures.

3. The apparatus of claim 1 further comprising a means for interpreting received light, which is in communication with the first light detector and the second light detector, from the first light detector and the second light detector for calculating a light reflectance factor and the reflectance zone has a concave configuration.

4. The apparatus of claim 3 wherein the reflectance zone has a concave configuration.

5. An apparatus comprising
a reflectance head comprising a body that defines a reflectance zone and a plurality of apertures;
at least a first light source and a second light source in opposing positions and at least a first light detector and a second light detector inserted into the reflectance head apertures, wherein the light sources correspond to opposing light detectors; the first light source and the second light detector are in different planes; and
a means for interpreting received light, which is in communication with the light detectors, from the at least first and second light detectors for calculating a light reflectance factor.

6. The apparatus of claim 5 wherein the reflectance head comprises a tetrafluoroethylene fluorocarbon polymer.

7. The apparatus according to claim 6, wherein the at least first and second light sources are positioned at different illumination angles relative to the surface of the effect-particle-containing material.

8. The apparatus of claim 7 wherein the reflectance zone has a concave configuration.

9. The apparatus according to claim 5, wherein the at least first and second light sources are positioned at the same illumination angle relative to the surface of the effect-particle-containing material.

10. A process for measuring effect-particle orientation in a continuous process comprising
(a) illuminating a surface of an effect-particle-containing material using incident beams of light in opposing directions over substantially the same given area wherein the incident beams of light are emitted in both upstream direction and downstream direction of an apparatus which comprises a reflectance head, a plurality of apertures, a first light detector, and a second light detector;
(b) measuring incident light reflectance from the effect-particle-containing material in opposing directions;
(c) determining a first absolute value of a difference between the opposing reflectance measurements at corresponding angles to obtain a first absolute value;
(d) comparing the first absolute value to a second absolute value obtained from a known standard; and optionally
(e) manipulating the effect-particle orientation to minimize, maximize or otherwise adjust the difference between the first and second absolute values.

11. The process according to claim 10 comprising the manipulating step.

12. The process of claim 11 wherein the measuring is conducted continuously or intermittently.

13. The process of claim 11 wherein the measuring is conducted intermittently.

14. The process of claim 13 wherein the effect-particle comprising a surface which comprises a material illuminated with a non-visible light.

15. The process of claim 14 wherein the light is near-infrared radiation.

16. The process of claim 15 wherein the light has a wavelength of about 940 nm.

17. The process of claim 16 wherein illumination of the surface of the effect-particle-containing material using incident beams of light occurs in opposing machine directions.

18. The process of claim 17 wherein the effect-particle-containing material comprises paint, film, coating, coated article, or polymer.

19. The process of claim 10 wherein the measuring is conducted continuously or intermittently.

20. The process of claim 10 wherein the measuring is conducted continuously.

21. The process of claim 20 wherein the effect-particle comprises a surface which comprises a material illuminated with a non-visible light.

22. The process of claim 21 wherein the light is near-infrared radiation.

23. The process of claim 10 wherein illumination of the surface of the effect-particle-containing material using incident beams of light occurs in opposing machine directions.

* * * * *